United States Patent [19]
DeCaria et al.

[11] Patent Number: 5,245,090
[45] Date of Patent: Sep. 14, 1993

[54] TWO-STAGE CLEAVAGE OF CUMENE HYDROPEROXIDE

[75] Inventors: Anthony J. DeCaria, Murrysville; Alain A. Schutz, Penn Township, Westmoreland County, both of Pa.

[73] Assignee: Aristech Chemical Corporation, Pittsburgh, Pa.

[21] Appl. No.: 943,666

[22] Filed: Sep. 11, 1992

[51] Int. Cl.$^5$ .................................. C07C 37/08
[52] U.S. Cl. ........................... 568/798; 568/385
[58] Field of Search ................. 568/798, 385, 397

[56] References Cited

U.S. PATENT DOCUMENTS

| | | | |
|---|---|---|---|
| 2,957,921 | 10/1960 | Adams et al. | 260/621 |
| 3,441,618 | 4/1969 | Flickinger | 260/621 |
| 4,310,712 | 1/1982 | Langley | 568/798 |
| 4,358,618 | 11/1982 | Sifniades et al. | 568/385 |
| 4,434,305 | 2/1984 | Kurosaka et al. | 568/768 |
| 4,480,134 | 10/1984 | Fulmer | 568/385 |
| 5,017,729 | 5/1991 | Fukuhara et al. | 568/798 |

Primary Examiner—Werren B. Lone
Attorney, Agent, or Firm—William L. Krayer

[57] ABSTRACT

This invention is an improved two-stage method for producing phenol and acetone from cumene hydroperoxide (CHP) comprising decomposing cumene hydroperoxide in a first stage, and subjecting the product of the first stage to hydrogenation in a second stage; residual cumene hydroperoxide may be decomposed in the second stage, with or without recycling of acetone and/or part of the effluent of the second stage back to the first stage; cumene is also desirably recycled.

31 Claims, 2 Drawing Sheets

Figure 1:
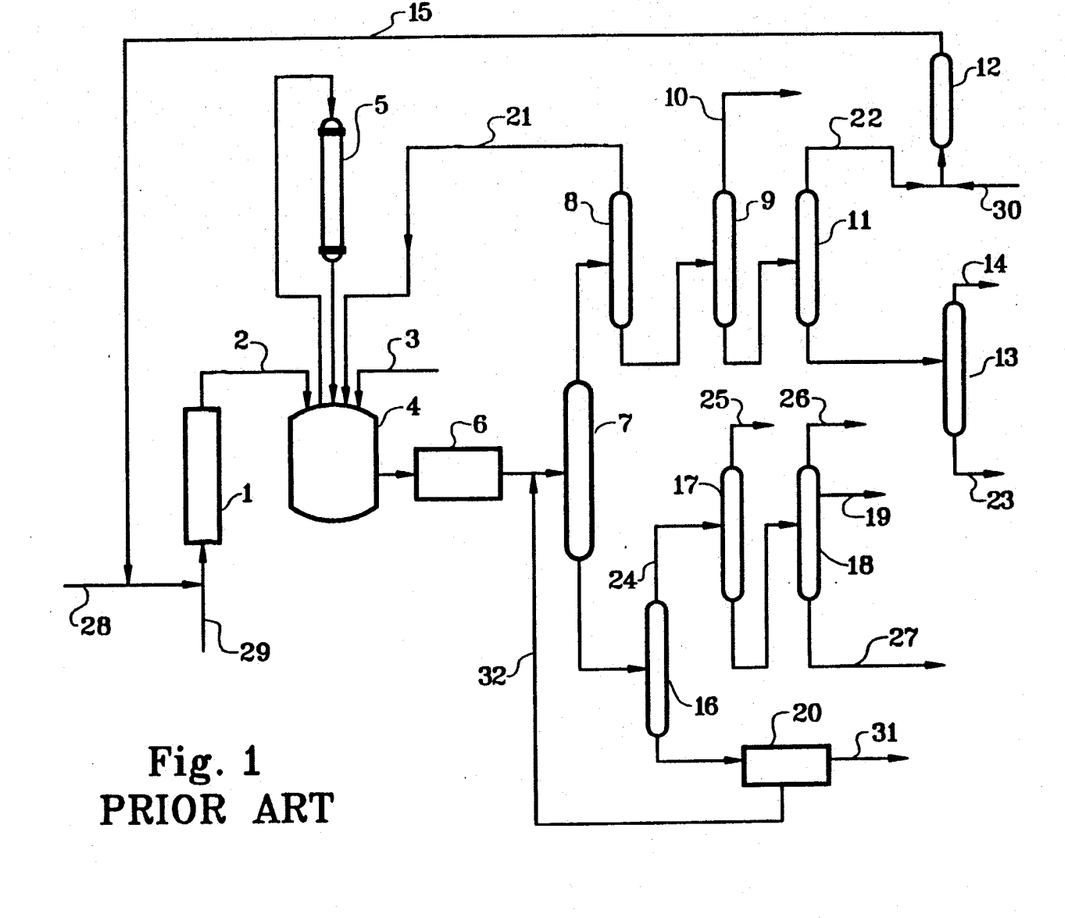

Fig. 1
PRIOR ART

Fig. 2

TWO-STAGE CLEAVAGE OF CUMENE HYDROPEROXIDE

TECHNICAL FIELD

This invention is an improved two-stage method for producing phenol and acetone from cumene hydroperoxide (CHP) comprising decomposing cumene hydroperoxide in a first stage, and subjecting the product of the first stage to hydrogenation in a second stage; residual cumene hydroperoxide may be decomposed in the second stage, with or without recycling of acetone and/or part of the effluent of the second stage back to the first stage; cumene is also desirably recycled.

BACKGROUND OF THE INVENTION

The method of making phenol by oxidation of cumene and catalytic cleavage of the resulting cumene hydroperoxide is well known and has replaced most of the phenol processes based on chlorination or sulfonation of benzene. More than five billion pounds per year of phenol capacity is now available in the world based on this technology.

A typical process consists of a cumene oxidation section, a CHP concentration operation, an acid-catalyzed cleavage reaction generally carried out in a fully back-mix reactor, and a product neutralization and recovery section.

Many improvements directed to increasing the yield and purity of the products have been disclosed in the patent literature. Also, many disclosed methods describe the use of heterogeneous catalysts for replacing sulfuric acid or other mineral acids which are now less desirable because of environmental regulations. Some improvements have also been made in the recovery of phenol, cumene and alpha-methylstyrene (AMS) from the waste products.

Methods using various acid catalysts are described in U.S. Pat. Nos. 2,718,172; 2,626,281; 3,187,052; 3,376,352; 4,016,213; 4,209,465; 4,267,380; 4,743,573; 4,870,217; 4,849,387; 4,490,565; 4,490,566; 4,898,987; and 4,898,995. Heterogeneous catalytic cleavage has to be carried out in either a fixed bed reactor or in a back-mix slurry reactor. As a result of the high exothermicity of the cleavage reaction and its relatively high rate of reaction, it is rather difficult to use a fixed bed reactor for this reaction. On the other hand, using a back-mix slurry reactor poses its own problems, namely, catalyst recovery and recycle, catalyst attrition, and mass transfer limitations at high conversions. In addition, catalyst deactivation can lead to unstable levels of CHP in the reactor which can lead to a runaway reaction.

Improvements to maximize the reaction yield have been primarily related to the reactions of the by-product AMS. It is formed in the cleavage reactor from the dehydration of dimethylbenzylalcohol (DMBA), which in turn is generally the largest by-product of the oxidation step. AMS is either recovered as a product or hydrogenated to cumene after it has been separated from phenol and acetone. Another major by-product is acetophenone which is usually not recovered. While acetophenone is inert under normal cleavage conditions, AMS can react with itself to form dimers or higher polymers or it can react with phenol to form cumyl phenol.

Where an increased yield of AMS is desired, it is maximized by maximizing DMBA conversion while minimizing the AMS side reactions. Methods for improving the AMS yield (minimizing side reactions) include adding acetone as a solvent to dilute the AMS or using alternative reactor configurations. Some of these methods are described in U.S. Pat. Nos. 2,663,735; 2,957,921; 2,757,209; 2,748,172; 3,376,352; 3,626,281; 3,187,052; 4,310,712, and 4,207,264. As these side reactions are consecutive and as the "desired" product AMS is the intermediate product, the reactor of choice for maximizing AMS yield is the plug flow reactor because of its low hold back value. This is incongruous with the ideal CHP cleavage reactor where it is desired to operate at a constant low CHP concentration and a high hold back value.

From these considerations was derived the concept of the two-stage cleavage reactor as described in U.S. Pat. Nos. 2,757,209 and 4,358,618. In these processes, CHP is incompletely converted in a first-stage back-mix reactor. Under these conditions, DMBA is only partially dehydrated to AMS so that the AMS concentration is kept low and its side reactions are minimized. Also, unreacted CHP condenses with DMBA to form dicumylperoxide (DiCup). The second-stage reactor consists of a tubular reactor operating essentially as an ideal plug flow reactor. In this reactor, residual CHP is cleaved to phenol and acetone, DiCup is decomposed to phenol, acetone and AMS, and residual DMBA is dehydrated to AMS. As a result of the kinetics of the plug flow reactor, higher yields of AMS can be obtained. However, the reactor must be designed for precisely the optimum residence time in order to maximize the AMS yield. Too short of a residence time will lead to unconverted DMBA and DiCup while too long of a residence time will result in conversion of additional AMS to heavies.

Numerous methods have been disclosed for removing by-products and purifying acetone and phenol produced from cumene oxidation. Some such methods are described in U.S. Pat. Nos. 2,748,172; 2,663,735; 2,790,549; 3,043,883; 3,140,318; 3,155,734; 3,187,052; 3,376,352; 3,965,187; 4,480,134; 4,626,600, and 4,722,769. These processes are primarily related to the removal of benzene from acetone and the separation of acetol, mesityl oxide, and other potential color bodies from phenol.

U.S. Pat. Nos. 2,715,145 and 4,960,958 report improvements in the recovery of phenol, cumene, and AMS from heavy ends. U.S. Pat. No. 3,441,618 discloses a method by which phenol distillation residue is selectively hydrogenated in order to produce better quality phenol, e.g. phenol with better stability toward discoloration when chlorinated. In this process, AMS is hydrogenated to cumene for recycle.

For each of these improvements, the basic concept of the CHP cleavage process remains the same. The goal is to maximize the yield of AMS regardless of whether the AMS is recovered as a separate product or hydrogenated to cumene and recycled. The maximum AMS yield lies within the range of 70-80% based on the DMBA in the feed to the cleavage step.

The present invention obviates many of the known problems of the cumene processes by providing higher phenol yields, less energy consumption, easier product purification, better product quality, and reduction of waste products including waste water.

SUMMARY OF THE INVENTION

Our improved process for carrying out the catalytic decomposition of cumene hydroperoxide containing dimethylbenzylalcohol (DMBA) as an oxidation by-product in accordance with this invention comprises the following steps: (a) mixing the cumene hydroperoxide with an acid catalyst (no more than about five milliequivalents of hydrogen ion per liter of reaction volume) in a well mixed reactor, preferably a (conventional) back-mix reactor, operating the reactor at a temperature of about 170°–190° F. for a time sufficient to effect decomposition of at least about 95% (typically about 95% to about 99%) of the CHP to phenol and acetone while at the same time converting no more than about 25% of the DMBA to alpha-methyl styrene to make AMS in an amount no more than about 1.2 wt. % of the contents of the reactor; (b) reacting the product from the initial reactor in a second reactor containing a hydrogenation catalyst, and operating the second reactor under hydrogenation conditions, preferably at a temperature of about 150°–250° F. with a molar flow rate of hydrogen equivalent to 1–4 times the molar flow rate of DMBA in the original CHP feed to the initial reactor and a hydrogen pressure of from 50 to 150 psig, allowing sufficient contact time in the second reactor to effect essentially complete decomposition of the residual CHP to phenol and acetone and over 95% disappearance of the DMBA and DiCup and to effect virtually complete hydrogenation of AMS (both AMS present in the feed to the fixed bed reactor and AMS formed from the reaction of DMBA and DiCup) to cumene. The process can be run to accomplish hydrogenation and decomposition of residual CHP simultaneously or in sequence, with or without the recycle of a portion of the acetone product to the back-mix reactor, and with or without the recycle of a portion of the product from the fixed bed reactor to the back-mix reactor; cumene may also be recycled.

In this manner, the concentration of AMS which is the major source of the heavy by-products from the cleavage reactions is at all times kept to a minimum and AMS is essentially eliminated from the final reaction product. By reducing the amount of AMS present in the reactors, the amount of AMS-polymers and cumyl phenol formed is substantially reduced. The cumene which is formed from the hydrogenation of AMS can be recovered and recycled to the oxidation reactors thus improving the overall yield of the process.

The CHP feed we use will have been made by the oxidation of cumene and will typically contain, by weight, about 83% to about 89% CHP, about 7–10% cumene, about 3.5–5.5% DMBA, and about 0.5–1.5% acetophenone.

DETAILED DESCRIPTION OF THE INVENTION

FIG. 1 is a flow sheet or schematic diagram of a conventional (prior art) phenol process based on single-stage CHP cleavage. CHP is produced from the partial oxidation (by oxygen from line 29) of cumene (fed through line 28) in the oxidation reactor 1. The CHP, which contains some DMBA and acetophenone, is fed through inlet 2 to the back-mix cleavage reactor 4. An acid catalyst, such as sulfuric acid, is also fed to reactor 4 through inlet 3. As the cleavage of CHP proceeds, heat is evolved which boils some of the acetone product produced from the cleavage reaction. This acetone is condensed in condenser 5 and refluxed to the cleavage reactor 4. The effluent from the cleavage reactor 4 passes through an acid neutralizer 6 and then is sent on to a splitter column 7 to separate the crude acetone and phenol products.

The crude acetone separated in splitter column 7 is first passed to an acetone topping column 8 where a portion of the acetone is separated out and recycled back through line 21 to the cleavage reactor 4. This provides dilution of the AMS produced in the cleavage reactor 4 thereby reducing the amount of AMS by-products produced. The crude acetone is then further refined in column 9 to produce a finished acetone product in line 10. The bottoms of column 9 contain cumene and AMS. This stream is passed to column 11 which separates the cumene from the AMS. Most conventional phenol plants have facilities for either recovering AMS as a purified product or hydrogenating AMS to cumene and recycling the cumene. Sometimes both facilities are present. Thus, some AMS can be distilled overhead with the cumene in column 11. The overhead stream is then passed through line 22 to a hydrogenation reactor 12 where it is contacted with hydrogen from line 30 over a hydrogenation catalyst, preferably in a fixed bed. The AMS in the feed is converted to cumene and the effluent cumene stream 15 is recycled to the oxidation reactor 1. The crude AMS stream from the bottom of column 11 is passed to column 13 where it is refined into a product AMS 14. Heavies from column 13 are carried in line 23 for burning as fuel.

The crude phenol is passed to column 16 where it is separated from the bulk of the heavy by-products. The overhead phenol stream 24 from column 16 is passed through columns 17 and 18 where it is refined into a purified phenol product 19. The heavies are sent from column 16 to a cracking unit 20 in which additional phenol and AMS are obtained. They may be recycled to splitter 7 by way of line 32. The residue from the cracking unit 20 is sent to fuel in line 31; lines 25, 26 and 27 are purges.

What we have discovered is that by proper selection of catalyst and conditions, the hydrogenation of AMS to cumene which is normally part of the conventional process can be accomplished selectively prior to the separation of the AMS from the acetone and phenol products. By selectively we mean that the AMS can be hydrogenated without significantly hydrogenating either the acetone or the phenol products. Our process is essentially a two-stage CHP cleavage process in which the first stage is operated in such a manner as to minimize the formation of AMS while the second stage is also a hydrogenation reactor operated to convert AMS to cumene as quickly as the AMS is introduced and/or formed in the second stage. In this manner, the concentration of AMS in both cleavage stages is always low and as a result the formation of AMS by-products (AMS polymers and cumyl phenol) is also kept at a minimum.

Figure 2:
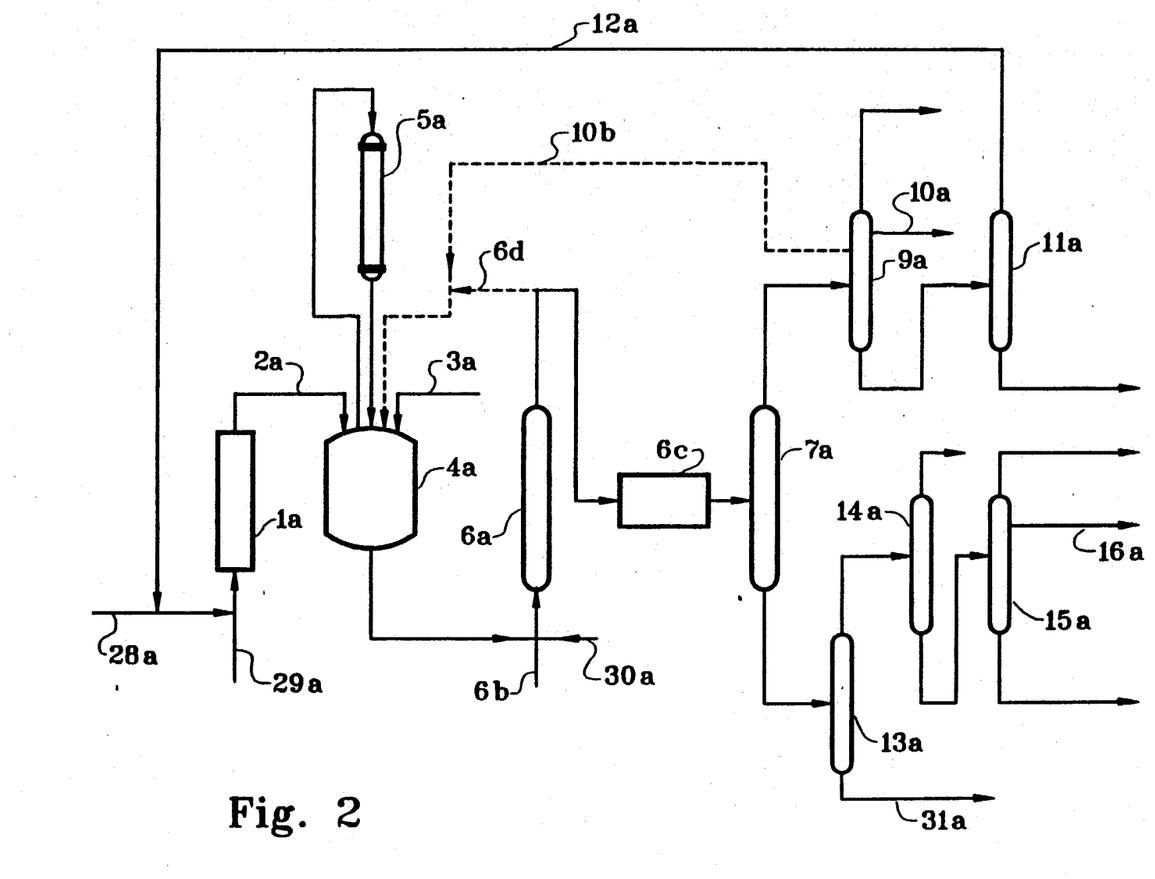

A flow sheet or a schematic diagram of our two-stage phenol process is given in FIG. 2. Once again CHP containing some DMBA is produced in reactor 1a by partially oxidizing cumene introduced through line 28a with oxygen from line 29a. The CHP is fed to reactor 4a through inlet 2a where it is mixed with acid which is fed through inlet 3a. The heat of reaction is removed by partially boiling the acetone product which is condensed in heat exchanger 5a and refluxed to the reactor. Up to this point, the apparatus (but not the process) is identical to the conventional cleavage technology; however, the cleavage reactor 4a is operated at a much lower acid concentration than the corresponding reactor 4 in the conventional technology of FIG. 1. Typical conditions for the conventional reactor 4 of FIG. 1 are: temperature of from 170° to 190° F., acid concentration from 20 to 40 milliequivalents of hydrogen ion per liter of reaction volume, and residence time of from 10 to 20 minutes. Typical conditions for the first-stage reactor 4a of the two-stage process of our invention are: temperature of from 150° to 190° F., acid concentration of about 0.5 (or other effective amount) to 5 milliequivalents and preferably about 0.5 to 1 milliequivalent of hydrogen ion per liter of reaction volume, and a residence time of from 10 to 20 minutes. Thus, the first stage of the two-stage process operates at an order-of-magnitude or more lower acid concentration than the conventional single-stage cleavage reactor. It was shown previously in U.S. Pat. No. 4,358,618 that under these conditions the CHP conversion is incomplete, although from 95% to 99% of the CHP is converted to phenol and acetone. An important result from the standpoint of the present process is that very little dehydration of DMBA to AMS takes place. Under these conditions, only about 10% to 20% (generally no more than 25%) of the DMBA in the feed is converted to AMS. As much as 70% of the DMBA combines with CHP to form dicumylperoxide (DiCup) and some of the DMBA remains unreacted. Another important result is that only minor amounts of heavies (AMS polymers and cumyl phenol) are formed.

In the case of sulfuric acid, the appropriate hydrogen ion concentration is provided by about 25 ppm to about 250 ppm sulfuric acid, based on weight. For other homogeneous catalysts, generally acids, their strengths can be calculated by their ionization constant.

The product from the first-stage reactor 4a is pumped to the second-stage reactor 6a which is a packed bed reactor. Here the crude product is contacted with a hydrogenation catalyst in the presence of hydrogen from line 30a. The unreacted CHP quickly decomposes to form phenol and acetone. The small amount of AMS which was produced in the first-stage reactor is quickly converted to cumene before it has sufficient time to further react to form heavies. The DiCup which was formed in the first-stage reactor is decomposed under the influence of the acid, still in the reaction product from vessel 1a, to form AMS, phenol, and acetone. Additional acid (line 6b in FIG. 2) can be added between the first and second stages to increase the rate of decomposition of DiCup. The AMS which is thus formed is also rapidly converted to cumene by action of the hydrogenation catalyst before it has sufficient time to form heavies. In this manner, the AMS concentration, and thus the driving force for the formation of AMS polymers and cumyl phenol, is kept to a minimum.

Optionally, a portion of the product stream from second stage reactor 6a may be recycled through line 6d to dilute the AMS in reactor 4a.

The remainder of FIG. 2 shows how the process can simplify the downstream processing and recovery of products. As in the conventional process of FIG. 1, the crude product must be neutralized in vessel 6c before further processing. This can be greatly simplified in the two-stage process because the acid concentration is much lower. The concentration of acid in our process can be sufficiently low that the neutralized crude product can be sent directly to distillation without acid extraction or phase separation, resulting in salt production no higher than is ordinarily obtained after acid extraction. After neutralization, the crude phenol and acetone products are split in splitter column 7a. Another advantage of our process is that it produces considerably less acetol (1-hydroxy-2-propanone, or hydroxyacetone) than older processes, enabling a reduction in size of splitter column 7a, compared to conventional systems. Since acetone recycle to the first-stage reactor is no longer required, the acetone topping column (column 8 in FIG. 1) is no longer necessary. The acetone is refined into a pure product in column 9a and recovered in line 10a. Some of it may be recycled through line 10b to dilute the concentration of AMS in reactor 4a. The bottom stream from column 9a contains cumene and some heavies. The heavies are separated from the cumene in column 11a and a cumene recycle stream 12a is recycled back to the oxidation reactor 1a. The AMS product column (column 13 in FIG. 1) is no longer required. The crude phenol stream from column 7a is sent to column 13a where the bulk of the heavies are removed in line 31a. Since the amount of AMS polymers and cumyl phenol is much lower than in the conventional process, heavy ends cracking (cracking unit 20 in FIG. 1) may be considered optional depending on local economics. As in the conventional process, the crude phenol is further refined in columns 14a and 15a to obtain a pure phenol product at 16a. Thus, the two-stage cleavage process, among other advantages, results in the elimination of two distillation columns and the heavy ends cracking step in the product recovery area, and may reduce or eliminate acid extraction and result in downsizing of the splitter column.

By operating at relatively mild reaction conditions compared to the conventional process and also as a result of the hydrogenation step in the second-stage reactor, other by-products such as acetol as well as color formers are greatly reduced. This simplifies the refining steps illustrated in FIG. 2 and results in recovery of a purer product.

The key feature of our two-stage process which distinguishes it from other two-stage processes is the hydrogenation of AMS in the second-stage reactor. One key to the success of the process is to quickly hydrogenate essentially all of the AMS which forms in the reactors to cumene without hydrogenating the desired products, acetone and phenol. Due to the relative ease with which AMS is hydrogenated, selective hydrogenation of AMS can be achieved over a fairly wide range of conditions. For any given hydrogenation catalyst, these conditions can be determined by appropriate experiments. A second key to the success of the process is maintaining a proper balance between the rate at which AMS is hydrogenated and the rate at which AMS is formed from the dehydration of DMBA and the decomposition of DiCup. The rate at which AMS is hydrogenated should be at least equal to and preferably greater than the rate at which AMS is formed in order to prevent a buildup of AMS in the second-stage reactor which would lead to formation of high amounts of AMS by-products. However, it has been found that under certain conditions DiCup can be hydrogenated in the second-stage reactor.

When DiCup is hydrogenated, it forms two moles of DMBA. The two moles of DMBA are subsequently dehydrated to form two moles of AMS which in turn are hydrogenated to two moles of cumene. In this manner, a mole of DiCup is converted to two moles of cumene. If we consider the first-stage reaction in which the DiCup was formed by combining DMBA with CHP, the overall effect of the hydrogenation of DiCup is the conversion of one mole of DMBA and one mole of CHP from the original CHP feed to two moles of cumene. While it is desired to convert the DMBA to cumene, it is not desired to convert CHP to cumene. While not affecting the overall yield of the process, it does represent an additional cost to the process in terms of extra hydrogen usage and energy costs related to the recovery and recycle of the additional cumene. Thus, it is desired to maintain the lowest possible concentration of AMS in the second-stage reactor while minimizing the hydrogenation of DiCup.

The hydrogenation of DiCup in the second-stage reactor 6a can be minimized by proper adjustment of the process parameters to give the desired balance between the rate of acid catalyzed decomposition of DiCup and the rate of hydrogenation of the AMS which is formed from this decomposition. While high hydrogenation activity can lead to substantial hydrogenation of DiCup, low hydrogenation activity will lead to high levels of AMS in the second-stage reactor and thus high heavies formation. Hydrogenation activity can be adjusted by varying the type and amount of the hydrogenation catalyst used, the support material, the hydrogen flowrate and pressure, and the temperature, as well as hydrogen concentration and pressure. The rate of acid catalyzed decomposition of DiCup can be adjusted by varying the type and amount of acid catalyst used and the temperature. The amount of acid catalyst can be varied by adding additional acid catalyst (line 6b in FIG. 2) between stages to increase the decomposition rate of the DiCup. Another way of increasing the decomposition rate is by using an acidic support (such as a super acid, resin, or silica/alumina) for the hydrogenation catalyst. This has the added advantage of maintaining a very low homogeneous acid level in the crude product which is convenient in terms of the downstream processing. By a "super acid", we mean a "super acid" catalyst as generally described in the literature as an acid system which is stronger than concentrated sulfuric acid. As the acidity of the support material increases, the rate of decomposition of the DiCup will increase. As a result, the rate of hydrogenation of AMS must be increased to keep pace with the increased rate of formation of AMS.

In practice, the balance between the hydrogenation rate of AMS and the decomposition rate of DiCup is monitored by monitoring the mass balance of DMBA and DMBA derived by-products (i.e. AMS polymers, cumyl phenol, and cumene). The CHP feed 2a to the first-stage reactor 4a is analyzed by liquid chromatography to determine the total molar flowrate of DMBA entering with the CHP feed. The effluent from the second-stage reactor 6a is analyzed by gas chromatography to determine the total molar flowrates of AMS polymer, cumyl phenol, and cumene leaving this reactor. The equivalent molar flowrate of DMBA is determined by adding the individual molar flowrates of these three constituents. The molar flowrate of the AMS polymers is added twice since two moles of DMBA are required to form one mole of the polymer (polymers consist primarily of dimers). Under the desired operating conditions, AMS and DiCup are essentially completely converted so that the equivalent molar flowrate of DMBA in the effluent from the second-stage reactor should equal the molar flowrate of DMBA in the CHP feed. If the hydrogenation rate is slow compared to the rate of decomposition of the DiCup, then this will lead to a buildup of AMS in the second-stage reactor 6a and result in a large amount of AMS polymers and cumyl phenol in the effluent from the second-stage reactor. On the other hand, if the rate of hydrogenation is too high with respect to the rate of decomposition of DiCup, then some DiCup will be hydrogenated to form additional DMBA. Thus the equivalent DMBA measured in the effluent from the second-stage reactor will be greater than the DMBA in the CHP feed to the first-stage reactor. The difference in these molar flowrates is a measure of the amount of DiCup hydrogenated. As stated above, the appropriate process parameters can be adjusted to maintain the desired balance between the yield of desired products (i.e. minimization of heavies) and the formation of extra cumene from the hydrogenation of DiCup. The optimum balance is a function of economic considerations (i.e. value of additional yield versus cost of recycling extra cumene and cost of extra hydrogen consumption).

Sulfuric acid is the most common choice of catalyst for use in conventional cleavage reactors, and we also prefer it. However, as taught in U.S. Pat. No. 4,358,618 other catalysts can be used to obtain the same or similar results in the first-stage reactor such as: sulfur dioxide, perchloric acid, toluene sulfonic acid, and Lewis acids such as boron triflouride or aluminum chloride. Even heterogeneous acid catalysts can be used in the first-stage reactor. By the same results, we mean 95 to 99% conversion of CHP to phenol and acetone and no more than 25% conversion of DMBA to AMS. The strength of a particular acid will determine the amount of acid required to achieve these results. For each acid, this can be determined by appropriate experiments.

Palladium catalysts have been found to work well in the second-stage reactor, but other hydrogenation catalysts may be used as well such as: platinum, ruthenium, and copper. As outlined above, for any given catalyst process parameters must be adjusted to give the desired balance balance between AMS hydrogenation and DiCup decomposition. Palladium catalysts have worked well for the following ranges of conditions: temperature of from 150° to 250° F., liquid hourly space velocity (LHSV) of from 5 to 10 liters/hr/liter catalyst, hydrogen pressure of from 50 to 150 psig, and a hydrogen molar flowrate of from 1 to 4 times the molar flowrate of the DMBA in the the original feed to first-stage reactor 4a. For other hydrogenation catalysts, the process conditions can be determined by appropriate experiments, but are not expected to be greatly different than the conditions for palladium.

We have also discovered an alternative mode of operation in which DiCup is totally eliminated from the reaction scheme. According to this operating mode, the first-stage reactor is operated at the high end of our acid concentration range (3 to 5 milliequivalents of hydrogen ion per liter of reaction volume instead of the otherwise preferred 0.5 to 1 milliequivalent) to effect essentially complete decomposition of the CHP in the first stage. In terms of sulfuric acid, the concentration is about 100 ppm to about 200 ppm based on the CHP feed comprising about 83 to about 89% CHP, about 7 to about 10% cumene, about 3.5 to about 5.5% DMBA, and about 0.5 to about 1.5% acetophenone, said CHP feed having been made by the oxidation of cumene. Under these conditions of relatively high acid concentration, DiCup is not formed. Normally this type of operation would lead to a large amount of heavies formation in the first stage as a result of a large amount of AMS formation; however, the AMS formed is diluted, and thus the formation of heavies is minimized, by recycling a portion of the effluent from the second-stage reactor back to the first-stage reactor. Since all of the AMS is converted to cumene in the second stage, the recycle stream contains no AMS. In this way, the AMS in the first stage is diluted to lower concentrations thus decreasing the amount of heavies formed. By operating in this mode, the decomposition of the CHP and the hydrogenation of the AMS are completely segregated (i.e. all of the CHP is decomposed in the first stage and all of the AMS is hydrogenated in the second stage). Since no CHP or DiCup is passed to the second stage, the hydrogenation of CHP or DiCup is totally eliminated. This optional recycle operating mode is illustrated by stream 6d in FIG. 2, shown as a dotted line.

An even further reduction in heavies formation may be achieved by using an acidic support in the second stage and operating in the recycle mode described above. Using an acidic support enables the first stage to be operated at the lower end of the acid concentration range for which a small amount of CHP will remain unreacted and a small amount of DiCup will be formed. Fine tuning of conditions in the second stage (i.e. balancing hydrogenation and acidic activity as described above) will result in selective conversion of the DiCup to cumene, phenol, and acetone in the second stage. A proper balancing of conditions in the two stages leads to the lowest combination of AMS and acid concentration which in turn leads to the lowest heavies formation. The procedure for balancing the reactor conditions is the same as described above (i.e. based on DMBA balance).

Our invention will be illustrated in the following examples:

APPARATUS—A bench scale version of the two-stage cleavage/hydrogenation process was set up in a laboratory, which included components 2a, 3a, 4a, 5a, 6a, 6b, 6c, and 30a of FIG. 2. The unit consisted of a feed tank and pump for delivering CHP to the first stage, a feed burette and pump for delivering sulfuric acid catalyst to the first stage, a 100 ml jacketed backmix reactor with integral acetone condenser for the first stage, a transfer pump between stages, a jacketed ½-inch diameter reactor for the second stage, and a hydrogen delivery system for the second reactor. A water bath was used to heat the first-stage reactor while an oil bath was used for heating the second-stage reactor. A vacuum controller was provided with the first-stage reactor to control temperature, while a pressure controller was provided with the second-stage reactor to control the hydrogen pressure. Collection vessels were provided for collecting and sampling the effluent from each reactor.

EXAMPLE 1

The first-stage reactor was operated under the following set of conditions:

| Temperature | 177° F. |
| Residence Time | 12 minutes |
| Acid Concentration | 0.1 wt % |
| Recycle Acetone | 11.1% of feed |

These conditions represent the optimum conditions for operating a single-stage conventional CHP cleavage reactor. Therefore the results of this test were considered to establish a baseline from which the merits of the two-stage process could be judged. Previous tests had shown excellent agreement between the lab reactor and the full-scale plant reactor.

A convenient method for comparing the results of various operating modes is to compute the pounds of waste products produced per 100 pounds of phenol product. The results will be divided into wastes directly associated with AMS (AMS dimers and cumyl phenol), other lights (lighter than DMBA), and other heavies (heavier than DMBA) which are not directly related to AMS. In addition, acetol will be listed separately since it plays an important role in the phenol purification.

The results for the baseline case are listed below:

| Waste | lbs per 100 lbs phenol |
|---|---|
| AMS Dimers | 1.53 |
| Cumyl Phenol | 1.50 |
| Acetol | 0.31 |
| Other Lights | 0.17 |
| Other Heavies | 1.98 |
| Total | 5.49 |

EXAMPLE 2

Using the same apparatus as Example 1, the second-stage reactor was packed with 60 ml (34.6 g) of a hydrogenation catalyst comprising 0.5% Pd on carbon granules (20–70 mesh). The catalyst was obtained from Englehard and is a commercially available catalyst. The catalyst was reduced by flowing hydrogen over the catalyst for several hours at 90° C. and 100 psig.

The first-stage reactor was operated at the following set of conditions: 1 atm, 189° F., 31 ppm sulfuric acid, 11.1 wt % acetone in the feed, and 15 minutes residence time. Conditions in the second-stage reactor were: 92 psig hydrogen pressure, 200° F., 4.2 liters/hr/liter catalyst LHSV, and 442 sccm hydrogen flow.

The steady-state results are listed below for comparison to the baseline run:

| Waste | lbs per 100 lbs phenol |
|---|---|
| AMS Dimers | 0.37 |
| Cumyl Phenol | 0.77 |
| Acetol | 0.16 |
| Other Lights | 0.34 |
| Other Heavies | 2.11 |
| Total | 3.75 |
| Cumene from CHP | 4.33 |

A reduction of over 30% in the total waste products may be seen to have been effected by hydrogenating AMS in the second-stage reactor. AMS dimers and cumyl phenol are reduced to about ½ the amount obtained in the baseline experiment.

Also listed in the results is the quantity of cumene obtained from the hydrogenation of unreacted CHP from the first-stage reactor. This represents an additional cost for the two-stage process since it requires extra hydrogen consumption. This number will be used as an additional point of comparison between alternative two-stage processes.

EXAMPLE 3

The second-stage reactor was packed with 50 ml (45.8 g) of a hydrogenation catalyst consisting of 0.5 wt % Pd on 1/16-inch alumina spheres. The catalyst was obtained from Calsicat and is commercially available. The catalyst was reduced overnight with hydrogen at 150° C. and 100

The first-stage reactor was run at the following set of conditions: 1 atm, 189° F., 25 ppm sulfuric acid, 11.1 wt % acetone in the feed, and 15 minutes residence time. Conditions in the second-stage reactor were: 105 psig hydrogen pressure, 248° F., 5.0 liters/hour LHSV, and 286 sccm hydrogen flow rate.

The steady-state results are listed below:

| Waste | lbs per 100 lbs phenol |
|---|---|
| AMS Dimers | 0.29 |
| Cumyl Phenol | 0.46 |
| Acetol | 0.13 |
| Other Lights | 0.65 |
| Other Heavies | 1.59 |
| Total | 3.12 |
| Cumene from CHP | 6.40 |

A reduction in total waste products of 43% was achieved and the AMS dimers and cumyl phenol were reduced to ¼ that of the base case. Conversion of CHP to cumene, however, was higher than that obtained with Pd on the carbon support.

EXAMPLE 4

This run was made with the same catalyst as that of Example 3. The first-stage conditions were as follows: 1 atm, 188.4° F., 17 ppm sulfuric acid, no acetone in the feed, and 15 minutes residence time. Conditions in the second stage were: 100 psig hydrogen pressure, 251.0° F., 5.0 liters/hr/liter catalyst LHSV, and 286 sccm hydrogen flow rate.

The steady-state results are listed below:

| Waste | lbs per 100 lbs phenol |
|---|---|
| AMS Dimers | 0.39 |
| Cumyl phenol | 0.80 |
| Acetol | 0.16 |
| Other Lights | 0.55 |
| Other Heavies | 1.34 |
| Total | 3.24 |
| Cumene from CHP | 4.78 |

The overall amount of waste products was about the same as that in Example 3. However, by operating without acetone dilution in the feed, the AMS dimers and especially the cumyl phenol increased from their levels in Example 3. The hydrogenation of CHP to cumene was markedly reduced compared to Example 3.

EXAMPLE 5

This run was made with the same catalyst as that of Example 3. The first-stage conditions were as follows: 1 atm, 189.5° F., 62 ppm sulfuric acid, 11.1 wt. % acetone in the feed, and 15 minutes residence time. Conditions in the second stage were: 100 psig hydrogen pressure, 243° F., 7.6 liters/hr/liter catalyst LHSV, and 290 sccm hydrogen flow rate.

The steady-state results are listed below:

| Waste | lbs per 100 lbs phenol |
|---|---|
| AMS Dimers | 0.35 |
| Cumyl Phenol | 0.64 |
| Acetol | 0.19 |
| Other Lights | 0.88 |
| Other Heavies | 1.07 |
| Total | 3.13 |
| Cumene from CHP | 3.48 |

The reduction in waste products is about the same as that of Example 3. However, by operating at a much higher acid concentration in the first stage and a shorter residence time in the second stage, the hydrogenation of CHP to cumene was further reduced to nearly ½ from that obtained in Example 3.

EXAMPLE 6

The examples recited thus far have shown a substantial reduction in the waste products from the conventional single-stage technology at the expense of hydrogenating some of the CHP to additional cumene. By properly balancing the rate of CHP decomposition with the rate of AMS hydrogenation, the conversion of CHP to cumene can be reduced. One way that this can be achieved is by supporting the hydrogenation catalyst on an acidic support.

Such a catalyst was prepared in the laboratory using a "super acid" support. The support material was prepared by reacting sulfuric acid with zirconium oxide and then calcining at temperatures above 600° C. This material was then impregnated with 1 wt. % Pd. The second-stage reactor was packed with 41.5 ml (56 g) of this catalyst. The catalyst was reduced overnight with hydrogen at 150° C. and 100 psig.

The first-stage reactor was run at the following conditions: 1 atm, 186.5° F., 46 ppm sulfuric acid, 11.1 wt. % acetone in the feed, and 13.3 minutes residence time. The second-stage conditions were: 100 psig hydrogen pressure, 180° F., 4.8 liters/hr/liter LHSV, and 75 sccm hydrogen flow rate.

The steady-state results are listed below:

| Waste | lbs per 100 lbs phenol |
|---|---|
| AMS Dimers | 0.47 |
| Cumyl phenol | 0.80 |
| Acetol | 0.14 |
| Other Lights | 0.27 |
| Other Heavies | 1.67 |
| Total | 3.37 |
| Cumene from CHP | 0.88 |

The amount of waste products is only slightly greater than that obtained in Example 3. However, the hydrogenation of CHP to cumene was reduced to only 14% of that obtained in Example 3, and is sufficiently low to normally be of only minor economic consequence.

EXAMPLE 7

In the above examples, the reduction in waste products was achieved by minimizing the AMS concentration in the first-stage reactor. This, however, resulted in incomplete conversion of CHP which was then partially hydrogenated to cumene in the second-stage reactor. A way to completely eliminate conversion of CHP to cumene is to operate the first-stage reactor under conditions in which essentially all of the CHP is reacted in this stage. This, however, would normally lead to high concentrations of AMS and subsequently to high yields of waste products.

To achieve both goals (reduction of wastes along with elimination of CHP hydrogenation), a portion of the outlet from the second-stage reactor can be recycled back to the first-stage reactor in order to dilute the AMS concentration in that reactor. This is illustrated in FIG. 2 (line 6d). By operating the second-stage reactor at a much higher throughput than the feed rate to the first-stage reactor, any desired dilution of the AMS in the first-stage reactor can be achieved. In this manner, the AMS concentration is reduced regardless of the degree of conversion of CHP. Therefore, the first-stage reactor can be operated at conditions sufficient to provide essentially complete conversion of the CHP.

The second-stage reactor was packed with the same catalyst as that of Example 3. The first-stage reactor was operated at the following conditions: 1 atm, 187.1° F., 150 ppm sulfuric acid, 11.1 wt. % acetone in the feed, and a 15 minute residence time based on the flow rate of the feed. The second-stage reactor was run at the following conditions: 90 psig hydrogen pressure, 182.1° F., 16 liters/hr/liter LHSV, and 184 sccm hydrogen flow rate. At these conditions, the flow rate through the second stage was twice the flow rate of fresh feed to the first stage.

The steady-state results are listed below:

| Waste | lbs per 100 lbs phenol |
| --- | --- |
| AMS Dimers | 0.55 |
| Cumyl Phenol | 0.91 |
| Acetol | 0.13 |
| Other Lights | 0.26 |
| Other Heavies | 1.62 |
| Total | 3.50 |
| Cumene from CHP | 0.00 |

Under the conditions in the first-stage reactor, essentially all of the CHP was converted. As a result, there was no hydrogenation of CHP to cumene in the second stage. The dilution of AMS in the first stage by recycling the flow from the second stage resulted in a substantial reduction in waste products, although the wastes were slightly higher than in Example 3.

EXAMPLE 8

In Example 6, a "dual function" catalyst was used to establish a balance between the rate of decomposition of DiCup in the second stage and the rate of hydrogenation of AMS. An alternative way of establishing this balance is to adjust the acid level in the second-stage reactor by adding more acid (line 6b in FIG. 2). Since some AMS is formed in the first stage, it is desirable to hydrogenate this AMS to cumene prior to the acid addition. Otherwise, the higher acid level in the second stage would result in excessive conversion of this AMS to heavies. This can be done by dividing the second stage into two beds of catalyst with addition of acid between the beds. The first bed is small and provides just enough contact time to hydrogenate the AMS from the first stage. A negligible amount of DiCup is converted in this bed. The second catalyst bed is larger. More acid catalyst is added between the beds to increase the decomposition rate of DiCup in this second bed.

According to this scheme, two catalyst beds were packed with the 0.5 wt. % Pd on alumina catalyst. This is the same catalyst which was used in Example 3. The first bed contained 10 ml (8.41 g) of catalyst while the second bed contained 72.5 ml (67.33 g) of catalyst. A pressurized feed tank with a connecting capillary tube was used to add acid between the two beds of catalyst.

The first-stage conditions were as follows: 1 atm, 187° F., 53 ppm sulfuric acid, 11.1 wt. % acetone in the feed, and 13.3 minutes residence time. The second-stage conditions were: 100 psig hydrogen pressure, 194° F., 1150 ppm sulfuric acid in second catalyst bed, 40 hr$^{-1}$ LHSV in the first catalyst bed, 5.5 hr$^{-1}$ LHSV in the second catalyst bed, and 75 sccm hydrogen flow rate.

The steady-state results are listed below:

| Waste | lbs per 100 lbs phenol |
| --- | --- |
| AMS Dimers | 0.25 |
| Cumyl Phenol | 0.71 |
| Acetol | 0.17 |
| Other Lights | 0.43 |
| Other Heavies | 1.59 |
| Total | 3.15 |
| Cumene from CHP | 1.16 |

The results are comparable to the results obtained with the "dual function" catalyst in Example 6. The amount of acid added between beds can be adjusted as the hydrogenation activity of the Pd catalyst changes with time. However, the acid level required in the second catalyst bed to decompose the DiCup is about as high as that required for typical single-stage CHP cleavage.

Thus, it may be seen that our invention is a method of making phenol and acetone from cumene comprising decomposing cumene hydroperoxide, CHP, containing dimethyl benzyl alcohol, DMBA, as a by-product in a first-stage reaction zone in the presence of no more than about 5 milliequivalents of hydrogen ion per liter of solution homogeneous acid catalyst, thereby producing phenol, acetone, and no more than about 1.2 wt. % alpha methyl styrene from the dehydration of DMBA with much of the DMBA combining with CHP to form dicumylperoxide, DiCup; contacting the product of said first-stage reaction zone with hydrogen in the presence of a hydrogenation catalyst to hydrogenate at least a portion and preferably all of said alpha methyl styrene by-product to cumene, while at the same time decomposing DiCup to acetone, phenol, and AMS, said AMS also being hydrogenated to cumene, and recovering phenol and acetone from the reaction product so contacted while recycling the cumene to produce more cumene hydroperoxide.

We claim:

1. Method of making phenol and acetone from cumene hydroperoxide containing dimethylbenzyl alcohol comprising feeding cumene hydroperoxide containing dimethylbenzyl alcohol to a first-stage reaction zone having a first-stage reaction volume, decomposing at least 95% of the cumene hydroperoxide in said first-stage reaction zone by contacting it with an acid catalyst which provides an effective amount up to about 5 milliequivalents of hydrogen ion per liter of reaction volume, thereby producing a first-stage reaction mixture including (a) phenol, (b) acetone, (c) up to about 1.2 wt. %, based on the contents of said first-stage reaction volume, of alpha methyl styrene by dehydration of dimethylbenzyl alcohol, (d) residual dimethylbenzyl alcohol, (e) dicumylperoxide by combination of cumene hydroperoxide and dimethylbenzyl alcohol, and (f) residual cumene hydroperoxide, contacting said first-stage reaction mixture, in a second-stage reaction zone, with hydrogen in the presence of a hydrogenation catalyst to hydrogenate alpha methyl styrene to cumene, at the same time or thereafter contacting said first-stage reaction mixture with an acid catalyst to decompose residual cumene hydroperoxide to phenol and acetone, dehydrate residual dimethylbenzyl alcohol to alpha methyl styrene, and decompose dicumylperoxide to acetone, phenol and alpha methyl styrene, and recovering phenol and acetone from the product of said second-stage reaction zone.

2. Method of claim 1 in which said acid catalyst is sulfuric acid.

3. Method of claim 1 in which said acid catalyst is sulfur dioxide.

4. Method of claim 1 in which said acid catalyst is perchloric acid.

5. Method of claim 1 in which said acid catalyst is toluene sulfonic acid.

6. Method of claim 1 in which said acid catalyst is a Lewis acid.

7. Method of claim 1 in which said hydrogenation catalyst is a supported palladium catalyst.

8. Method of claim 7 in which the support for said hydrogenation catalyst is acidic.

9. Method of claim 7 in which the support for said hydrogenation catalyst is carbon.

10. Method of claim 7 in which the support for said hydrogenation catalyst is alumina.

11. Method of claim 7 in which hydrogen is added to said second-stage reaction zone at a rate of about 1 to 4 times the molar flowrate of dimethylbenzyl alcohol in the cumene hydroperoxide feed to said first-stage reaction zone.

12. Method of claim 2 wherein the sulfuric acid concentration in said first-stage reaction mixture is about 30–50 parts per million.

13. Method of claim 1 wherein the acid concentration in said first-stage reaction zone provides about 0.5 to about 1.0 milliequivalents of hydrogen ion per liter of first-stage reaction mixture.

14. Method of claim 2 wherein the concentration of sulfuric acid provides about 3 to about 7 milliequivalents of hydrogen ion per liter of cumene hydroperoxide feed.

15. Method of claim 1 wherein the residence time in said first-stage reaction zone is about 10 to about 20 minutes.

16. Method of claim 1 wherein at least a portion of acetone recovered from said product of said second-stage reaction zone is recycled to said first-stage reaction zone.

17. Method of claim 1 including separating cumene from the product of said second-stage reaction zone, recycling said cumene to an oxidation zone to make cumene hydroperoxide, and feeding said cumene hydroperoxide to said first-stage reaction zone.

18. Method of making phenol and acetone from cumene hydroperoxide made by the oxidation of cumene, comprising feeding to a first reaction zone a cumene hydroperoxide feed having been made by the oxidation of cumene, decomposing said cumene hydroperoxide to phenol and acetone by contacting said cumene hydroperoxide in said first reaction zone with an effective amount of an acid catalyst, contacting a product stream from said first reaction zone, which product stream includes alpha methyl styrene and residual cumene hydroperoxide, with hydrogen in a second reaction zone in the presence of a hydrogenation catalyst on an acidic support, thereby hydrogenating alpha methyl styrene in said second reaction zone to cumene and decomposing residual cumene hydroperoxide to acetone and phenol, recycling a portion of the reaction product of said second reaction zone to said first reaction zone, and recovering phenol and acetone from said second reaction zone.

19. Method of claim 18 wherein at least about 50% of said reaction product of said second reaction zone is recycled to said first reaction zone.

20. Method of claim 18 wherein about 66 to about 75% of said reaction product of said second reaction zone is recycled to said first reaction zone.

21. Method of claim 18 wherein said hydrogenation catalyst is palladium.

22. Method of claim 18 wherein said cumene hydroperoxide feed comprises, by weight, about 83 to about 89% cumene hydroperoxide, about 7 to about 10% cumene, about 3.5 to about 5.5% dimethylbenzyl alcohol and about 0.5 to about 1.5% acetophenone.

23. Method of claim 18 wherein the hydrogen is maintained in said second reaction zone in a concentration about 1 to 4 time the dimethylbenzyl alcohol concentration in said cumene hydroperoxide feed.

24. Method of claim 18 wherein the acid catalyst is sulfuric acid.

25. Method of claim 24 wherein the sulfuric acid is maintained.

26. Method of making phenol and acetone from cumene hydroperoxide made by the oxidation of cumene, comprising feeding to a first reaction zone a cumene hydroperoxide feed comprising, by weight, about 83 to about 89% cumene hydroperoxide, about 7 to about 10% cumene, about 3.5 to about 5.5% dimethylbenzyl alcohol and about 0.5 to about 1.5% acetophenone, said cumene hydroperoxide feed having been made by the oxidation of cumene decomposing said cumene hydroperoxide to phenol and acetone by contacting said cumene hydroperoxide in said first reaction zone with about 50 ppm to about 25 ppm, based on the cumene hydroperoxide feed, of sulfuric acid, contacting a product stream from said first reaction zone, which product stream includes alpha methyl styrene and up to about 1.2 wt. % cumene hydroperoxide, with hydrogen in a second reaction zone in the presence of a hydrogenation catalyst supported on an acidic support, thereby hydrogenating alpha methyl styrene in said second reaction zone to cumene, and at the same time decomposing residual cumene hydroperoxide to phenol and acetone, and recovering phenol and acetone from said second reaction zone.

27. Method of making phenol and acetone comprising contacting cumene hydroperoxide with an amount of hydrogen ion catalyst effective to decompose said cumene hydroperoxide to phenol and acetone up to about 7 milliequivalents of hydrogen ion catalyst per liter of cumene hydroperoxide, thereby forming a first reaction mixture, thereafter contacting said first reaction mixture with hydrogen in the presence of a hydrogenation catalyst to form a second reaction mixture, and recovering phenol and acetone from said second reaction mixture.

28. Method of claim 27 wherein said hydrogen ion catalyst is provided by sulfuric acid.

29. Method of claim 27 wherein said second reaction mixture is further treated with acid catalyst to decompose residual cumene hydroperoxide.

30. Method of claim 27 wherein said hydrogen ion catalyst is provided by a fluid acid.

31. Method of claim 27 wherein the hydrogenation catalyst is palladium and hydrogen is present in said second reaction mixture in a molar amount from 1 to 4 times the moles of dimethylbenzyl alcohol in said cumene hydroperoxide.

* * * * *

UNITED STATES PATENT AND TRADEMARK OFFICE
CERTIFICATE OF CORRECTION

PATENT NO. : 5,245,090
DATED : September 14, 1993
INVENTOR(S) : Anthony J. DeCaria and Alain A. Schutz It is certified that error appears in the above-indentified patent and that said Letters Patent is hereby corrected as shown below:

Column 11, line 8, after "100", insert --psig. --.
Column 16, line 45, change "25" to -- 250 --.

Signed and Sealed this

Twenty-second Day of March, 1994

Attest:

BRUCE LEHMAN

Attesting Officer    Commissioner of Patents and Trademarks